(12) United States Patent
Wider

(10) Patent No.: US 10,582,845 B1
(45) Date of Patent: Mar. 10, 2020

(54) VAGINAL SPECULUM

(71) Applicant: Elizabeth Joy Wider, Altadena, CA (US)

(72) Inventor: Elizabeth Joy Wider, Altadena, CA (US)

( * ) Notice: Subject to any disclaimer, the term of this patent is extended or adjusted under 35 U.S.C. 154(b) by 61 days.

(21) Appl. No.: 16/350,383

(22) Filed: May 19, 2017

(51) Int. Cl.
*A61B 1/32* (2006.01)
*A61B 1/303* (2006.01)
*A61B 1/00* (2006.01)

(52) U.S. Cl.
CPC ............ *A61B 1/303* (2013.01); *A61B 1/0011* (2013.01); *A61B 1/00066* (2013.01); *A61B 1/00096* (2013.01); *A61B 1/00103* (2013.01); *A61B 1/32* (2013.01)

(58) Field of Classification Search
CPC . A61B 1/303; A61B 1/00066; A61B 1/00096; A61B 1/00103; A61B 1/0011; A61B 1/32
See application file for complete search history.

(56) References Cited

U.S. PATENT DOCUMENTS

| | | | | |
|---|---|---|---|---|
| 3,132,645 A | * | 5/1964 | Gasper | A61B 1/32 600/184 |
| 2006/0129165 A1 | * | 6/2006 | Edoga | A61B 17/34 606/108 |
| 2008/0161644 A1 | * | 7/2008 | Ghabrial | A61B 1/00135 600/114 |
| 2011/0190579 A1 | * | 8/2011 | Ziarno | A61B 1/00016 600/109 |

* cited by examiner

*Primary Examiner* — Amy R Weisberg

(57) ABSTRACT

The present disposable vaginal speculum invention, a clear cylinder shaped one-piece speculum, which improves the visualization of the vaginal walls, aids in the location of the cervix, and decreases the discomfort of the traditional two blade vaginal speculum. This disposable vaginal speculum design results in the enhancement of vaginal wall and cervical analysis.

1 Claim, 2 Drawing Sheets

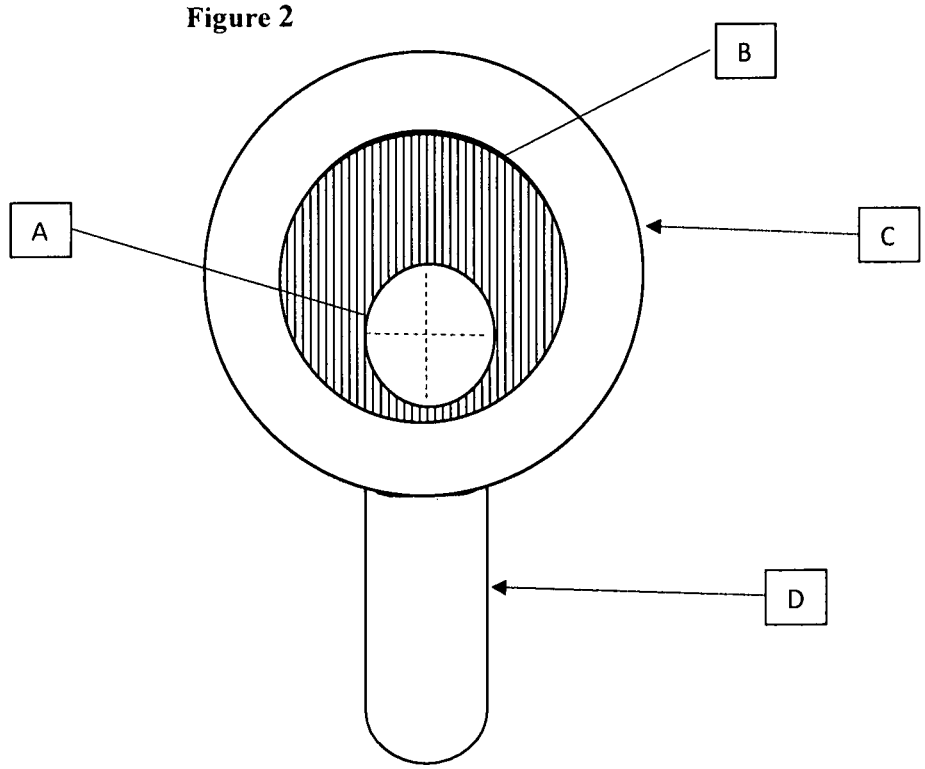

VAGINAL SPECULUM

BACKGROUND

Screening and treatment of vaginal and cervical cancerous and benign lesions are conducted with a vaginal specula. Currently, vaginal specula are two-bladed with a stationary blade with a handle and a pivoting blade for a linearly movement away from the stationary blade. These blades are limited to moving apart, then back together in relation to one axis.

The present disposable vaginal speculum invention addresses several significant disadvantages of the current two blade vaginal specula. First, the speculum is a one-piece clear cylinder shaped speculum which is more comfortable upon insertion to the circular os of the vagina. The two-bladed speculum is associated with "pinch points" along the sides of the blades, when the blades are opened and closed. The clear cylinder shape of the speculum also prevents the collapse of the vaginal walls, which obscures the visualization of the cervix that occurs with the two-bladed speculum, increasing the inspection of the vaginal walls upon insertion and removal. The tip of the present vaginal speculum has a clear perforated plastic film, which accommodates the location of the cervix prior to the use of the specimen collection brush or swab. Once the cervix is located, the specimen brush or swab can easily pierce the perforated plastic film to obtain the specimen, without disturbing the condition of the cervix. Lastly, the advantage of the present vaginal speculum invention, does not require additional dexterity for operation. The two-bladed speculum requires insertion and the use of the thumb to secure the position and maneuver for visualization.

SUMMARY

The present disposable vaginal speculum invention provides a new and unique design that eliminates existing disadvantages of the two-bladed speculum. This vaginal speculum invention is ideal as a comfortable and non-threatening devise, that provides a consistently accurate visualization of the vaginal walls and cervix, is universal for all body types and anatomy, easy and simple for clinician use, and cost effective to manufacture and use on an ongoing basis as a solid unit device.

The inventive disposable speculum with the present aspects of the invention includes a solid clear plastic non-latex device including a handle, circular rim, cylinder that decreased in size by 10% to the distal end, and perforated plastic film that will be manufactured in three sizes: small, medium, and large. All aspects of the present vaginal speculum invention provide increased patient comfort, ease of clinician use, and increased visualization of the vaginal walls and cervix for diagnostic purposes and specimen collection.

DESCRIPTION OF THE DRAWINGS

The following are the detailed description presented of the drawings.

FIG. 2: 2A-D is the end view of the speculum, 2A depicting 1A described above, 2B depicting 1B described above, 2C depicting 1C described above, and 2D depicting 1D described above.

Figure 1:
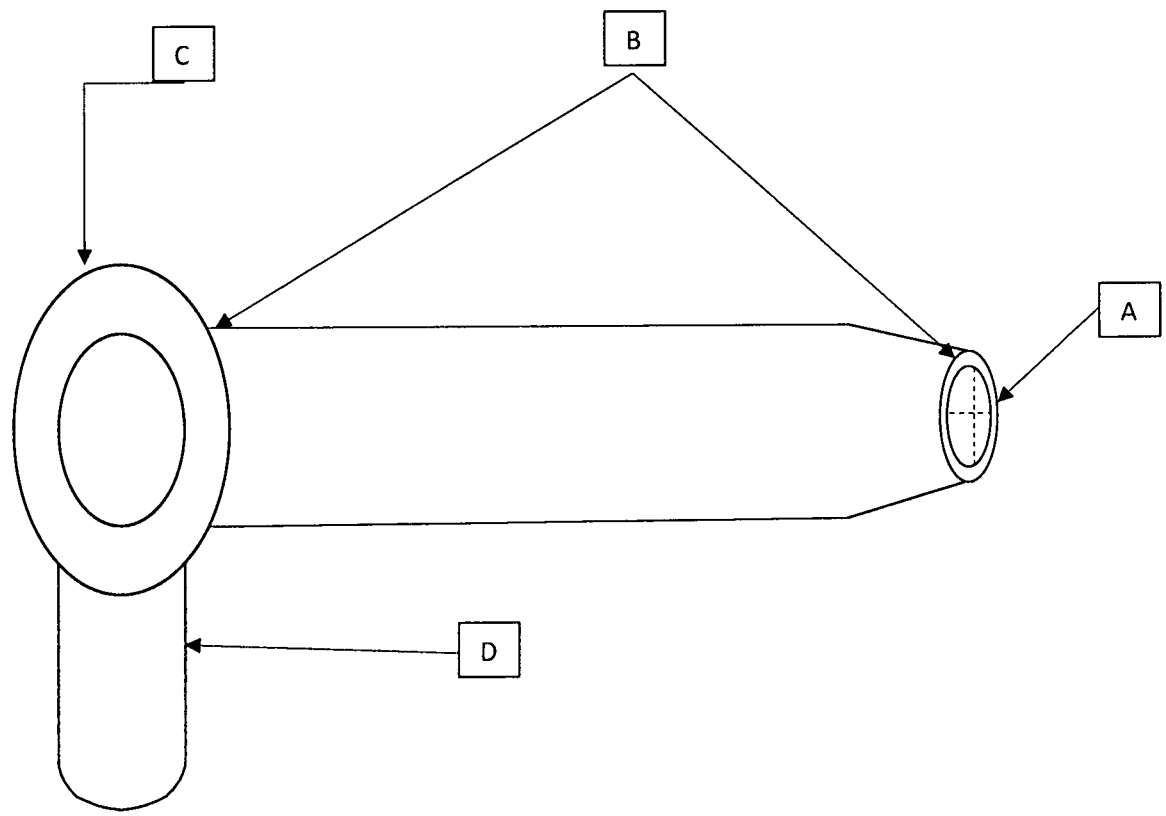
FIG. 1: 1A-D is a side view of the speculum. 1A is the approximately 1 mm thin plastic perforated film over the end of the speculum at a circumference of 4 inches for small, 4.5 inches for medium, and 5 inches for large. 1B is the clear approximately 2 mm thick cylinder of the plastic speculum that gradually decreases in diameter by 10% at the distal ½ inch end, a length of 6 inches for small, 7 inches for medium, and 8 inches for large. 1C is the 2 mm thick plastic circular posterior concaved ring-flared shield to limit insertion with a 1 inch width and inner circumference equal to size of small, medium and large sizes. 1D is the plastic handle attached to the speculum for insertion and maneuvering of the speculum at 3 inches long, with anterior concave shape, and 2 mm thick.

What is claimed:
1. A disposable plastic vaginal speculum, comprising:
   a. a solid clear cylinder configured to be placed within the vagina;
   b. an anterior concaved handle configured to be held by a clinician, said handle attached to a bottom of a circular concaved ring-flared shield configured to limit insertion of a proximal end of said solid clear cylinder and extending approximately normal to said solid clear cylinder;
   c. a clear film at a distal end of said solid clear cylinder;
   d. said clear film further comprising a cross-shaped perforation configured to permit the clinician to locate the cervix and to be easily perforated when the cervix is located by a specimen brush or swab without disrupting the cervical tissue;
   e. wherein said speculum comprises a single mold of the handle, ring and cylinder and said clear film is configured to be adhered to said cylinder with low heat.

* * * * *